United States Patent [19]

Johnson

[11] Patent Number: 5,705,175

[45] Date of Patent: Jan. 6, 1998

[54] NON-AQUEOUS CONTROLLED RELEASE INSECT REPELLENT AND INSECTICIDE GELS

[75] Inventor: Richard L. Johnson, The Woodlands, Tex.

[73] Assignee: Pennzoil Products Company, Houston, Tex.

[21] Appl. No.: 609,079

[22] Filed: Feb. 29, 1996

[51] Int. Cl.⁶ .................. A01N 25/04; A01N 25/10; A61K 9/10; A61K 47/32

[52] U.S. Cl. .................. 424/409; 424/486; 424/DIG. 5; 424/DIG. 10; 514/944; 514/919; 523/122

[58] Field of Search ................. 424/405, 409, 424/486, DIG. 5, DIG. 10, 40; 514/944; 523/122; 44/275; 252/315.1

[56] References Cited

U.S. PATENT DOCUMENTS

| 3,857,805 | 12/1974 | Prickril . | |
|---|---|---|---|
| 4,369,284 | 1/1983 | Chen | 524/476 |
| 4,469,613 | 9/1984 | Munteanu et al. | 252/92 |
| 4,812,309 | 3/1989 | Ong | 424/84 |
| 4,906,488 | 3/1990 | Pera | 426/573 |
| 5,132,355 | 7/1992 | Nahlovsky . | |
| 5,150,722 | 9/1992 | Rutherford | 131/335 |
| 5,208,038 | 5/1993 | Gressani et al. | 424/489 |
| 5,221,534 | 6/1993 | DesLauriers et al. | 424/78.03 |
| 5,316,744 | 5/1994 | Haehn et al. | 422/257 |
| 5,578,089 | 11/1996 | Elsamaloty . | |

FOREIGN PATENT DOCUMENTS

| 0 224 389 | 6/1987 | European Pat. Off. . |
| 224389 | 6/1987 | European Pat. Off. . |
| 5-345011 | 12/1993 | Japan . |
| WO 88/00603 | 1/1988 | WIPO . |
| WO 96/34077 A | 10/1996 | WIPO . |

OTHER PUBLICATIONS

Patent Abstracts of Japan, vol. 10, No. 276 (C-373), Sep. 10, 1998 and JP 61 098780 (Mitsui Petrochem Ind. Ltd, May 17, 1986.

*Primary Examiner*—Edward J. Webman
*Attorney, Agent, or Firm*—Lowe, Price, LeBlanc & Becker

[57] ABSTRACT

Controlled release insect repellent or insecticide based on a non-aqueous gel composition comprising from about 1 to about 20 weight percent of one or more diblock, triblock, radial block and/or multiblock copolymers, or a mixture thereof, based on synthetic thermoplastic rubbers. The ratio of the diblock copolymer to triblock, radial block and/or multiblock copolymer can be varied from about 0 percent to about 100 percent in either direction. The higher the triblock percentage, the stiffer the resultant gel. The material to be gelled is a hydrocarbon which based on its physical properties plays an important role in setting the controlled release rate. The composition of the hydrocarbon can vary in carbon chain length from an average of about C-13 to about C-30 and can vary in vapor pressure from about 2.3 mm Hg at 20° C. to less than about 0.1 mm Hg at 20° C. The hydrocarbon range on a weight basis is from about 65 to about 95 percent of the total weight of the gelled composition. The controlled release agent or active agent may comprise from about 0.1 to about 30 percent of the gel on a weight basis.

6 Claims, No Drawings

5,705,175

NON-AQUEOUS CONTROLLED RELEASE INSECT REPELLENT AND INSECTICIDE GELS

TECHNICAL FIELD

The invention relates to non-aqueous, controlled release polymer gels, and more particularly heterophase, thermally reversible hydrocarbon gels which are suitable for use in the controlled release of one or more insect repellents and/or one or more insecticides as an active substance.

The hydrocarbon gel of the invention contains block copolymers and/or blends thereof, the copolymers being preferably derived from styrene-rubber block units. The gels are useful for the controlled release of insect repellents and insecticides.

BACKGROUND ART

Controlled release agents have been used in the art in a variety of applications, including for the release of pheromones, insect repellents, animal repellents and pharmaceuticals.

For example, U.S. Pat. No. 4,469,613 discloses a detergent bar containing poly(ε-caprolactone) homopolymers and mixtures of poly(ε-caprolactone) homopolymers and other polymers (e.g. polyethylene or polypropylene). The detergent bar is disclosed as being useful in the controlled release of insect repellents, etc.

U.S. Pat. No. 4,812,309 discloses a gel comprising 14 to 22 percent α-hydro-Ω-hydropoly(oxyethylene)poly(oxypropylene(poly (oxyethylene)) block copolymer, additives, and 25 to 60 percent water, said to be effective as insecticide against cockroaches. However, this gel is not disclosed as providing for controlled release of the insecticidal agent and is of an aqueous nature.

U.S. Pat. No. 4,906,488 discloses modification of a permeant by the polymerization of monomers, prepolymers or polymers in the permeant liquid for controlled, sustained release.

U.S. Pat. No. 5,150,722 discloses a low density polyethylene/high density polyethylene copolymer for use in controlled release. Controlled release in the system described therein is affected by the use of a layered structure, with a core containing the agent to be released and a "burst layer" which confines the active substance from being prematurely released.

U.S. Pat. No. 5,208,038 discloses highly cross-linked particles for use as a carrier or adsorbent. Use of styrene and either divinylbenzene or tetraethylene glycol dimethacrylate are disclosed as being useful monomers for making such particles.

U.S. Pat. No. 5,316,744 discloses porous particles for controlled release of an active substance. The particles are blocked by use of a cross-linked hydrogel polymer, the blocking agent being sensitive to its physical environment.

Published Japanese Abstract JP 5345011 discloses an aromatiser composition obtainable in a pellet form. The composition is 100 parts hydrogenated block copolymer having 5 to 75 weight to weight a vinyl aromatic compound and a block of a conjugated diene previously hydrogenated to about 35%, and 3 to 200 parts aromatic substance.

Co-pending U.S. patent application Ser. No. 08/520,726 discloses a triblock, radial block and/or multiblock copolymer mineral oil gel useful as a candle. The gels disclosed may also optionally include a diblock copolymer.

U.S. Pat. No. 5,221,534 discloses gels having a mineral oil and blends of copolymers useful for health and beauty aid compositions.

International Patent Application No. WO88/00603 describes block copolymer compositions which are described as gels or gelloid liquid extended polymer compositions and which can comprise an intimate mixture of a block copolymer containing relatively hard blocks and relatively elastomeric blocks. The copolymer additionally has at least 500 parts by weight of extender liquid per 100 parts of the block copolymer, the liquid being present to extend and soften the elastomeric blocks of the block copolymer.

European Patent Application No. 224389 discloses styrene-diene block copolymer compositions and in particular a mixture of copolymers and a hydrocarbon oil.

U.S. Pat. No. 4,369,284 describes a transparent gel prepared from triblock copolymers and oils. The triblock copolymers therein give specific styrene end blocks to ethylene and butylene center blocks. The end block to ethylene and butylene center block ratio is given as being between 31:69 and 40:60. The polymer content in the Examples of U.S. Pat. No. 4,369,284 is from 5.9 to 25 percent.

Another known methodology for producing hydrocarbon containing gels includes the use of metal soaps, surfactants (microemulsions), homopolymers, ionic homo- and copolymers and block copolymers. Some common gelling agents are fatty acid soaps of lithium, calcium, sodium, aluminum, zinc and barium. A number of homo- and copolymers have been used to gel hydrocarbon systems at certain polymer treatment levels, including atactic ethylene-propylene. Homopolymers or copolymers that have pendant salt groups also form ion rich aggregates in a non-polar matrix. The ionic interactions and resultant polymer properties of these compositions, however, are dependent on the type of polymer backbone, type of ionic moiety and type of cation. Sulfonated polystyrenes exemplify this kind of system.

Surfactant combinations have also been used to gel mineral oil/water systems. Surfactants are generally used at about 30 weight percent to the gel oil and to gel about 1:4 oil/water mixtures. Non-ionic surfactants such as polyoxyethylene sorbitan monooleates exemplify this type of system.

It is one object of this invention to provide heterophase, thermally reversible hydrocarbon gel compositions that have advantageous properties when used as vehicle to solubilize or suspend an active substance insect repellent and/or insecticide and effect the controlled-release of said active substance.

A further object of the invention is to provide hydrocarbon gel compositions formed with certain diblock, triblock, radial block and/or multiblock copolymers which have advantageous properties when used as a non-aqueous, controlled release polymer gel.

It is a further object of the invention to provide methods of making a controlled release hydrocarbon polymer gel and articles of manufacture employing such gels.

Yet another object of the invention is to provide methods of using a hydrocarbon polymer gel blend of diblock, triblock, radial block and/or multiblock copolymers as a matrix for the controlled release of an active substance which is an insect repellent and/or an insecticide.

The advantages of the hydrocarbon gels of the invention, which are set forth below and, based upon this disclosure, will be recognized by those skilled in the art, are provided by use of heterophase, thermally reversible hydrocarbon gels as non-aqueous, controlled release gels.

SUMMARY OF THE INVENTION

The invention provides the above-mentioned objects and additional advantages evident herein in a non-aqueous, controlled release insect repellent and/or insecticide gel composition comprising:

(a) from about 65 to about 95 weight percent of a hydrocarbon;

(b) from about 1 to about 20 weight percent of a diblock, triblock, radial block and/or multiblock copolymer, or blends thereof comprising from about 0 to about 100 weight percent of one or more diblock copolymers and from about 100 to about 0 weight percent of one or more triblock, radial block and/or multiblock copolymers; and (c) from about 0.1 to about 30 weight percent, preferably from about 1 to about 10 weight percent, of an insect repellent and/or insecticide as an active substance.

The hydrocarbon of the composition preferably has a vapor pressure of from about 2.3 mm Hg to less than about 0.1 mm Hg at 20° C., as determined according to ASTM D2879-86. More preferred is a vapor pressure of from about 1.5 mm Hg to about 0.5 mm Hg at 20° C.

The invention further provides methods of making articles of manufacture that are controlled-release insect repellent or insecticide products, and methods of using the polymer hydrocarbon gels in these articles.

DETAILED DESCRIPTION OF THE INVENTION

The present invention provides a new non-aqueous, controlled release vehicle for the timed release of an insect repellent and/or an insecticide as an active substance. The controlled release vehicles are hydrocarbon-containing, block copolymer gels.

The non-aqueous, controlled release compositions of the invention comprise:

(a) from about 65 to about 95 weight percent of a hydrocarbon;

(b) from about 1 to about 20 weight percent of one or more diblock, triblock, radial block and/or multiblock copolymers, or blends thereof comprising from about 0 to about 100 weight percent of one or more diblock copolymers and from about 100 to about 0 weight percent of one or more triblock, radial block and/or multiblock copolymers; and (c) from about 0.1 to about 30 weight percent of an insect repellent and/or insecticide as an active substance.

In a preferred composition of the invention, the copolymers comprise from about 0.1 to about 30 weight percent, preferably from about 0.1 to about 10 weight percent, of one or more diblock copolymers, and from about 70 to about 99.9 percent triblock, radial block and/or multiblock copolymers.

When formed into gels, the copolymers or blends thereof comprise from about 1 to about 20 weight percent of the total weight of the composition. Preferably the total weight of polymer contained in the hydrocarbon will range from about 7 to about 18 weight percent, though this preference may change depending upon the particulars of the application desired, as apparent to one skilled in the art.

Each of the diblock, triblock, radial block and/or multiblock copolymers in the invention contains at least two thermodynamically incompatible segments. By the expression thermodynamically incompatible with respect to the polymers, it is meant that the polymer contains at least two incompatible segments, for example, at least one hard and one soft segment. In general, the ratio of segments in a triblock copolymer is one hard:one soft:one hard, known as an A—B—A copolymer. The multiblock and radial block copolymers may, however, contain any combination of hard and soft segments provided that there are both hard and soft segments present. Diblock copolymers, on the other hand, are of the A—B type and sequential with respect to the hard and soft segments.

Commercially available thermoplastic rubber type polymers which are especially useful in forming the compositions of the present invention are sold under the trademark Kraton® by Shell Chemical Company. The Kraton® rubber polymers are described as elastomers having an unusual combination of high strength and low viscosity and a unique molecular structure of linear diblock, triblock and radial block copolymers. Each molecule of the Kraton® rubber is said to consist of block segments of styrene monomer units and rubber monomer and/or comonomer units. Each block segment may consist of 100 or more monomer or comonomer units. The most common structure for a triblock copolymer is the above-mentioned linear A—B—A block type, with styrene-butadiene-styrene (SBS) and styrene-isoprene-styrene (SIS) being examples of the Kraton® D rubber series.

A second polymer series of this general type is the Kraton® G series. This copolymer comprises a styrene-ethylenebutylene-styrene type (S—EB—S) structure. The Kraton® G series is preferred in the practice of the invention, as the copolymers of this series are hydrogenated and thus more thermally stable; that is, decomposition is less likely to occur during blending of the G series polymers with the hydrocarbon (the D series polymers having unsaturation within the rubber block).

A particularly preferred triblock copolymer is Kraton® G-1650. Kraton® G-1650 is a S—EB—S triblock copolymer that has a specific gravity of about 0.91, and is said to have a tensile strength of about 500 psi as measured by ASTM method D-412 at a tensile jaw tester separation speed of 10 in./min. The styrene to rubber content of Kraton® G-1650 is said by the manufacturer to be about 29:71, and the Brookfield viscosity is about 8000 (toluene solution, cps at 77° F., 25% w). The Shore A hardness is about 75. It is preferred under the present invention that the end block to ethylene and butylene center block ratio in the triblock copolymer be less than 31:69.

The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber. This series of polymers is indicated as being a compounding ingredient or additive in adhesives, sealants and coatings, asphalt modification for roads and roofing, polymer modification, thermoset modification, and oil modification including use as viscosity index improvers, greases and gels.

The diblock copolymers include the AB type such as styrene-ethylenepropylene (S—EP), styrene-ethylenebutylene (S—EB), styrene-butadiene (SB) and styrene-isoprene (SI). A preferred diblock copolymer is Kraton® G-1702.

When formed into gels, the hydrocarbon comprises from about 65 to about 95 weight percent of the total weight of the composition. Preferably the total weight of the hydrocarbon contained in the composition will range from about 75 to about 95 weight percent, and more preferably will range from about 84 to about 93 weight percent. Most preferably the total weight of the hydrocarbon in the composition of the invention is about 90 weight percent, though this preference may change depending upon the particular application desired, as apparent to one skilled in the art.

While not being limited by theory, it is believed that the shorter the hydrocarbon chain length, the more volatile the hydrocarbon. Under the invention, the hydrocarbon is thought to act as a carrier for the active substance in the composition. Thus, in choosing a hydrocarbon for use in the invention, care must be taken to ensure that the hydrocarbon is sufficiently volatile at the temperature and pressure under which the invention is intended to operate. Additionally, the hydrocarbon must be of sufficient chain length to become suitably entwined within the polymer matrix, such that a desired gel consistency can be obtained for the particular application intended. Under these considerations, hydrocarbons useful in the practice of the invention are generally preferred to comprise an average of at least about 13 carbon atoms and of less than about 30 carbon atoms, and to have a vapor pressure of from about 2.3 mm Hg at 20° C. to about 0.1 mm Hg at 20° C.

The non-aqueous, controlled release gels of the invention all incorporate one or more active substances, such as insect repellents and insecticides and the like. Active substances are generally employed at from about 0.1 to about 30% by weight of the total gel composition. However, it is recognized by those skilled in the art that active substances can be used up to their characteristic solubility level when so desired.

Useful insecticides as an active substance in the invention include N-[[(4-chlorophenyl-)amino]carbonyl]-2,6-difluorobenzamide; 1,1'-(2,2,2-trichloroethylidene) bis(4-chlorobenzene); 2,2-dimethyl-1,3-benzodioxol-4-yl) methylcarbamate; O,O-diethyl-O-6-methyl-2-(1-methylethyl)-4-pyrimidinyl phosphorothioate; and O-ethyl-S-phenyl ethylphosphonodithioate. The insecticides may be of several types; Baits and Stomach Kills including Hydromethylnon (CAS-67485-29-4), Fenoxycarb (CAS-79127-80-3) and Avermectin; Residual Contact Kills such as synthetic Pyrethroids, including Permethrin (CAS-52645-53-1) and Cypermethrin (CAS-66841-24-5), Carbamates including Propoxur (CAS-114-26-1) and Carbaryl (CAS-63-25-2), Phosphorothioates such as Diazinon (CAS-333-41-5); Fumigant Kills including Organophosphates such as DDVP (CAS-62-73-7) and Chlorfeninphas (CAS-470-90-6), Crysanthemums including D-trans Allethrin; and Juvenile Hormones such as Methoprene (CAS-40596-69-8) and Hydroprene (CAS-41096-46-2).

Examples of insect repellents that serve as an active substance in the gels of the invention are N,N-diethyl-m-toluamide, commonly referred to as "DEET," for mosquitos and D-empenthrin for moths. These insect repellents and insecticides are illustrative of those active substances useful in the practice of the invention. Other active substance insecticides and insect repellents may be suitably used, as is known to those skilled in the art.

The gel consistency under the invention is controlled by varying the amount, ratio and types of certain polymers, preferably diblock, triblock, radial block and/or multiblock copolymers. The amount of each copolymer and the amount of the mixture contained in the hydrocarbon determines the final form of the gel. In general, the higher the copolymer content, the stiffer the gel. Additionally, the higher the amount of triblock, radial block and/or multiblock copolymer, the stiffer the gel. The gels under the present invention thus range from thin to stiff, as desired, and are generally transparent. The polymers under the invention provide gels which have desirable rheological properties and thus provide for a novel applications, particularly with respect to active substance insecticides and insect repellents that are sparingly soluble, if at all, in aqueous gels.

Product formation under the invention is achieved from block copolymers that form three-dimensional networks or gels through physical crosslinks. Crosslinking in these block copolymers occurs due to the formation of sub-microscopic particles of a particular block, referred to as domains. Crosslinking of the insoluble domains can be obtained by factors affecting the crosslink density of the networks including length of insoluble block domains, length of soluble block domains, and the number of crosslinkable sites. For example, branched or star polymers and other multiblock copolymers will have more crosslinks than triblock or diblock polymers. The type of solvent or plasticizer to which the blocks are subjected will also affect these characteristics.

Certain gels exhibit syneresis wherein the separation of liquid from the gel by contraction occurs by virtue of the concentration of the insoluble block present in the triblock copolymer. The higher the concentration of the insoluble block, as exemplified by styrene, the more phase separation and crosslinking will occur. However, according to this invention, the amount of syneresis which occurs can be controlled by mixing such systems with diblock, triblock, radial block and/or multiblock copolymers which do not exhibit syneresis.

A further advantage of the hydrocarbon gels of the invention is that the gel base is non-aqueous. As such, these gels are more readily used with non-aqueous active substances including, for example, organic compounds not readily soluble in aqueous controlled-release systems. The increased solubility further permits a greater concentration of many active substances than can be achieved using aqueous gel controlled release systems, thus making for products having stronger insect repellent and/or insecticidal activities, when desired. The gels additionally avoid the problems associated with emulsification of the active substance and the stability thereafter of the emulsified product.

In the preferred embodiment of the present invention, the polymer or polymer blend is formed in admixture with a carrier vehicle natural or synthetic hydrocarbon or mixtures thereof. In general any hydrocarbon comprising an average of from about 13 to about 30 carbon atoms is useful under the invention. Examples of suitable hydrocarbons are: peanut oil, paraffinic oil, isoparaffinic oil, a naphthenic oil, natural mineral oil and the like.

In a particularly preferred embodiment of the invention, the composition comprises a Kraton® triblock copolymer and, optionally, a Kraton® diblock copolymer, as described herein, in combination with a hydrocarbon and an active substance which is an insect repellent or an insecticide. For insect repellent sticks, gels, creams, lotions, etc., the particularly preferred repellant is N,N-diethyl-m-toluamide (DEET).

The non-aqueous controlled release gels of the invention are prepared by first heating the hydrocarbon to from about 65° C. to about 85° C. One or more triblock, radial block and/or multiblock copolymers, or mixtures thereof, and optionally one or more diblock copolymers, each in the desired amount is then slowly added to the hot hydrocarbon with agitation. The temperature of the mixture is held at from about 65° C. to about 85° C. for a time sufficient to dissolve the copolymer or blend thereof in the hydrocarbon. Mixing may be carried out in any conventional manner, and is again preferred at this stage. The polymer mix is sufficiently dissolved, generally in about 30 to 60 minutes, when the hydrocarbon/polymer mixture becomes clear and homogeneous.

The active substance is generally added to the gel in the desired amount at the cooling stage, just as the gel begins to form as judged by, for example, an increase in the viscosity of the mixture. Where the active substance is not particularly volatile, it may be added at any point during the process, but preferably at the cooling stage, and more preferably when gel formation begins, as described above. The gel is then allowed to cool to ambient temperature. On cooling, a clear gel forms which may have the consistency ranging from thin at low concentration of polymer to stiff at high polymer concentration.

In another embodiment of the invention, the hydrocarbon is first heated to from about 65° C. to about 85° C., at which point the copolymer mix is added to the desired weight percent as set forth herein. After sufficient time for the copolymer to dissolve in the oil, the composition is cooled and the active substance added, as above. The composition is then poured into a mold or a jar and is then allowed to further cool to form a gel. Similar variations in the methods of the invention as known to the skilled person in light of the present disclosure are within the scope of the present invention.

It is particularly preferred in making the controlled release gels of the invention to cool the polymer composition in a container or mold, depending upon the final application desired. The container may be any type suitable for the indicated use, as is generally known in the art. As examples of containers, conventional jars, thermoplastic housings, and the like, that are clear, colored or otherwise decorative are usefully employed for holding non-aqueous, controlled release gels under the invention. A mold is used to impart external features to the final products for those applications were such features are desired. Additionally, a mold may be used to impart a particularly shaped shape into the product. It is also within the scope of the present invention to cool the product in a container directly suitable for end use or compatible with a container suitable for end use.

The non-aqueous, controlled release gels of this invention may also contain one or more conventionally employed additives such as stabilizers, anti-oxidants, colorants, and the like to an extent not substantially affecting or decreasing the desired properties of the gel (i.e., the ability of the controlled-release gel to perform its intended function.) With respect to anti-oxidants, specific reference is made to BHT, which is generally employed at about 0.02 weight percent.

Colorants are useful in the invention when desired, as the gel composition is generally transparent. Thus, the gels of the invention can range from completely translucent to having a deep color, as desired, by control of the amount of colorant, if any, employed. The stiff gels may also be multicolored or have colored layers. Other design variations will be readily apparent to those skilled in the art in light of the present disclosure.

The following examples are presented to illustrate the invention and should not be considered as a limitation thereto. In these examples, parts are by weight per 100 weight parts of the composition (i.e. weight percent), unless otherwise indicated.

The diblock and triblock copolymers used in these examples are the preferred Kraton® polymers 1702 and 1650 described above and obtained from Shell Chemical Company. Penreco 2257 is a hydrocarbon with an average chain length of 14 carbons available from Pennzoil Products Company. Drakeol® 7 is a white mineral oil. Geahlene® 1600 comprises a mineral oil and polymer mixture best described by its CTFA definition: "mineral oil (and) hydrogenated butylene/ethylene/styrene copolymer (and) hydrogenated ethylene/propylene/styrene copolymer." Geahlene® 1600 is also available from Pennzoil Products Company.

EXAMPLE 1

In the preparation of a controlled release bait insect repellent gel, the following was prepared:

| | |
|---|---|
| Drakeol ® 7 Mineral Oil | 45.50 |
| Penreco 2257 | 10.00 |
| Peanut Oil | 27.00 |
| Polymer 1650 | 16.00 |
| Polymer 1702 | 0.50 |
| Hydromethylnon (CAS-67485-29-4) | 1.00 |

The hydrocarbon mixture is heated to about 75° C., after which the polymers, which have been blended, are slowly sifted in with constant agitation. The temperature is held for approximately 60 minutes to permit the polymer to dissolve in the hydrocarbons, thereby forming a clear mix, which is then allowed to cool. As the mixture begins to gel, the active is added with continued mixing. The gel is then allowed to further cool to ambient temperature to result in a stiff, translucent gel useful as an insect bait.

EXAMPLE 2

A residual insecticide gel was formed by admixture of the following:

| | |
|---|---|
| Geahlene ® 1600 | 99.00 |
| Permethrin | 1.00 |

The Geahlene® gel is heated to about 70° C. and mixed for approximately 45 min to obtain a melt. The mixture is allowed to cool. Permethrin is then added with mixing as the gel begins to reform, as above. A stiff, translucent gel forms that is useful as a residual insecticidal composition.

EXAMPLE 3

An insecticidal gel having volatile actives was prepared as follows:

| | |
|---|---|
| Isopar L (isoparaffinic oil) | 37.00 |
| Penreco 2257 | 40.50 |
| Polymer 1650 | 16.00 |
| Polymer 4702 | 0.50 |
| Active - Hydroprene | 5.00 |
| Active - Permethrin | 1.00 |

The hydrocarbons are first heated and the polymer blend slowly mixed in while maintaining the temperature as in Example 1. As the hydrocarbon/polymer mix cools and gellation begins, the actives are added with mixing. Upon complete cooling, a stiff gel forms that is useful as a volatile insecticide.

EXAMPLE 4

An insect repellent stiff gel, suitable for application to the skin of a user, was prepared from the following blend:

| | |
|---|---|
| Active - DEET | 10.00 |
| Cetearyl Octanoate | 5.00 |
| Cyclomethicone | 5.00 |
| Drakeol ® 7 Mineral Oil | 73.20 |
| Polymer 1650 | 6.45 |
| Polymer 1702 | 0.35 |

The oil and polymer blend are heated as in Example 1, cooled to the beginning of gellation, and the active substance added. After further cooling, a resultant hydrocarbon gel forms which is an insect repellent gel, suitable for application to the skin of a user.

I claim:

1. A non-aqueous, controlled-release insecticide composition comprising:
   (a) from about 65 to about 95 weight percent of a hydrocarbon;
   (b) from about 1 to about 20 weight percent of one or more diblock, triblock, radial block and/or multiblock copolymers, or a mixture thereof comprising from about 0 to about 100 weight percent of said one or more diblock copolymers and from about 100 to about 0 weight percent of said one or more triblock, radial block and/or multiblock copolymers; and
   (c) from about 0.1 to about 30 weight percent of one or more insecticides as an active substance.

2. The non-aqueous, controlled-release insecticide composition according to claim 1, wherein said active substance comprises from about 1 to about 10 weight percent.

3. The non-aqueous, controlled-release insecticide composition according to claim 1, wherein said hydrocarbon comprises an average of from about 13 to about 30 carbon atoms.

4. The non-aqueous, controlled-release insecticide composition according to claim 1, wherein said active substance is selected from the group consisting of bait, stomach kill, residual contact kill and fumigant kill insecticides.

5. The non-aqueous, controlled-release insecticide composition according to claim 1, wherein said active ingredient is selected from the group consisting of pyrethroids, carbamates, phosphorothioates, organophosphates, chrysanthemums and juvenile hormones.

6. A method for exterminating insects comprising:

providing a controlled release, stiff hydrocarbon gel comprising from about 65 to about 95 weight percent of a hydrocarbon; and, from about 1 to about 20 weight percent of one or more diblock, triblock, radial block and/or multiblock copolymers, or a mixture thereof comprising from about 0 to about 100 weight percent of said one or more diblock copolymers and from about 100 to about 0 weight percent of said one or more triblock, radial block and/or multiblock copolymers;

heating said controlled release hydrocarbon gel to form a substantially melted hydrocarbon/polymer mixture; and adding from about 0.1 to about 30 weight percent of an active substance, wherein said active substance is selected from the group consisting of one or more insecticides.

* * * * *